United States Patent [19]

Faktor et al.

[11] 4,028,207
[45] June 7, 1977

[54] MEASURING ARRANGEMENTS

[75] Inventors: Marc Marian Faktor, Bushey Heath; Thomas Ambridge, Harrow Weald; Ean Grant Bremner, Stanmore, all of England

[73] Assignee: The Post Office, London, England

[22] Filed: May 16, 1975

[21] Appl. No.: 578,144

[52] U.S. Cl. .......................... 204/195 R; 204/1 T; 204/129.2; 204/129.3

[51] Int. Cl.² .................. G01N 27/46; B23P 1/00

[58] Field of Search ........... 204/1 T, 195 R, 129.3, 204/129.2

[56] References Cited

UNITED STATES PATENTS

| | | | |
|---|---|---|---|
| 2,851,654 | 9/1958 | Haddad | 204/195 R |
| 3,117,899 | 1/1964 | McLouski | 204/195 R |
| 3,250,693 | 5/1966 | Amaya | 204/129.2 |
| 3,303,109 | 2/1967 | Just | 204/1 T |
| 3,379,625 | 4/1968 | Csabi | 204/1 T |
| 3,418,226 | 12/1968 | Marinace | 204/129.3 |
| 3,586,608 | 6/1971 | Juda et al. | 204/195 R |
| 3,660,250 | 5/1972 | Duffy | 204/1 T |
| 3,755,026 | 8/1973 | Reynolds | 204/195 R |
| 3,873,512 | 3/1975 | Latanision | 204/129.2 |

OTHER PUBLICATIONS

"Journal of Applied Electrochemistry", 1973, vol., 3, pp. 1–15.
"J. Phys. E: Sci. Instrum.", 1971, vol. 4, pp. 213–221.
"IEEE Trans. Electron Devices", 1969, Ed–16, pp. 445–449.

Primary Examiner—T. Tung
Attorney, Agent, or Firm—Kemon, Palmer & Estabrook

[57] ABSTRACT

The electrochemical measuring technique of the present invention employs, as the barrier material, a concentrated electrolyte, which also forms a medium for the controlled dissolution of a surface of the semiconductor so as to provide a continuous depth profile. The depth profile characteristic may be determined by capacitance-voltage measurements on n-type bulk GaAs, using KOH as the electrolyte.

5 Claims, 8 Drawing Figures

MEASURING ARRANGEMENTS

The invention relates to a measuring arrangement. The invention is particularly applicable to the determination of a characteristic of a semiconductor in which a measurable parameter which is related to said characteristic varies with depth in the semiconductor. The measuring arrangement employs an electrolyte as a 'Schottky' rectifying contact on a semiconductor, to provide a means of obtaining a profile of the carrier concentration within the semiconductor, to any required depth. This is achieved by using an anodic dissolution reaction, between the semiconductor and electrolyte, to controllably strip the semiconductor, whilst making simultaneous (or sequential) capacitance measurements on the depletion layer of the semiconductor, under reverse bias conditions. The capacitance is simply related to the carrier concentration by well established formulae (Schottky, 1942), so that straightforward analogue electronic circuitry permits the plotting of carrier concentration against depth.

The equipment operates briefly as follows:

For an $n$-type semiconductor, anodic dissolution takes place at a fixed potential (maintained by a potentiostatic controller), at a rate determined by the availability of minority carriers (holes), which are created by illuminating the material. The anodic potential is arranged to correspond to a band-bending of the order of 1 volt, in the depletion sense, enabling simultaneous capacitance measurement using phase-sensitive techniques. The integral of dissolution current, with a correction for depletion width, yields the depth scale of the profile plot. A control unit is included which either stops dissolution after the removal of a predetermined amount of material or allows the plotter pen to recycle. This means that the equipment may be left completely unattended whilst measurement takes place, after loading the sample, and making initial adjustments.

For a $p$-type semiconductor, large anodic currents are available without illumination, for small applied potentials. Dissolution could be performed either at constant potential, or under controlled constant current conditions. To obtain reverse bias conditions for capacitance measurements, periodic pulsing into the cathodic mode, to a predetermined potential would be used, with the restriction that only extremely small charge flow could be tolerated in the cathodic direction.

Automatic sensing to distinguish between $p$- or $n$- type material could be provided, by detecting the current, or capacitance, level under anodic operating conditions, and could then be used to set the appropriate conditions for depletion layer capacitance measurements.

An advantage of the electrochemical profile plotting system is the lack of restriction on depth. This distinguishes it from previous systems which require an increasing reverse bias potential to be applied to a Schottky barrier in order to extend the depletion width, and hence the measurement depth, as far as possible into the semiconductor. For these systems a limit is reached, beyond which no measurement is possible, when reverse bias breakdown occurs. For gallium arsenide this limit is, for example, about 3 $\mu$m and 0.1 $\mu$m at donor concentrations of $10^{16}$ and $10^{18}$ cm$^{-3}$ respectively. To probe more deeply requires removal of material in separate chemical etching steps, so that the process is no longer continuous. The automatic electrochemical system, however, performs the etching and measurement accurately and simultaneously (with the Schottky barrier always biassed well below critical breakdown voltage), to provide a continuous profile with no limitation on depth.

An additional feature is the possible application to the profiling of junction structures (p-n, n-p, p-n-p, and n-p-n) for which material removal is an essential requirement, and hence for which the previous systems are particularly inappropriate.

The electrochemical system could also be used to distinguish between different semiconductors (e.g. in profiling heterostructures) by providing a plot of band-bending potential, derived from capacitance measurement, against depth. More accurate measurement of the band-gap of materials might be obtained by analysis of the photocurrent characteristics of the semiconductor-electrolyte interface as a function of illumination wavelength.

The basic concepts have been verified for n- and p- GaAs and GaP using 10% w/v KOH electrolyte, and there is no intrinsic reason to prevent the technique from being extended to other materials.

The methods, apparatus, techniques and systems of measurement according to the invention are particularly useful in the determination of donor concentration profiles in semiconductor epitaxial layer/substrate structures (n/n$^+$), for use in IMPATT and other microwave diodes, which has been greatly simplified by means of an electrochemical technique of the present invention. Unlike previous methods, the invention provides a continuous depth profile which includes the entire interface region, and the substrate itself to any required depth. Thus by means of the invention information is obtained which is not only needed for checking against specific device requirements, but also for optimizing layer growth procedures.

The present invention, in common with known techniques, relies upon the formation of a Schottky barrier at the measured surface. A disadvantage of the methods and technique of the prior art is that the maximum depth below the surface from which information can be derived, such as by analysis of capacitance-voltage or current-voltage relationships, is strictly limited. This limitation arises because measurements are made upon the depletion region of the semiconductor, under reverse bias, and the extent of this region is governed by the maximum potential that may be applied before breakdown occurs. Since the active region thickness of an IMPATT diode is necessarily greater than the depletion width at breakdown, an epitaxial layer structure intended for such a device cannot be profiled as deeply as the interface region, without removal of surface material. Also, since the maximum depletion width decreases with increasing doping level, profiling through the interface into the substrate would require many steps, using the known method, which involves step-by-step removal by etching. It is therefore an object of this invention to enable the provision of continuous depth profile measurement, which is not possible from the known methods using evaporated metal dots, or a mercury probe.

The electrochemical technique of the present invention employs, as the barrier material, a concentrated electrolyte, which also forms a medium for the controlled dissolution of a surface of the semiconductor so as to provide a continuous depth profile. The depth profile characteristic may be determined by capacitance-voltage measurements on n-type bulk GaAs, using KOH as the electrolyte. In one method of electrochemical dissolution, according to the invention, the sample surface is illuminated through the electrolyte, whilst the Schottky barrier potential is maintained at a sufficiently low value to avoid breakdown. The illumination provides minority carriers which are essential for the dissolution reaction, so that the dissolution rate depends directly upon the illumination level. In order to obtain donor concentration profiles in epitaxial layer structures, a system, described below, has been developed in which capacitance measurements are made continuously while the epitaxial layer is dissolved electrochemically.

The invention will now be described, by way of example, with reference to the accompanying drawings in which.

Figure 1:
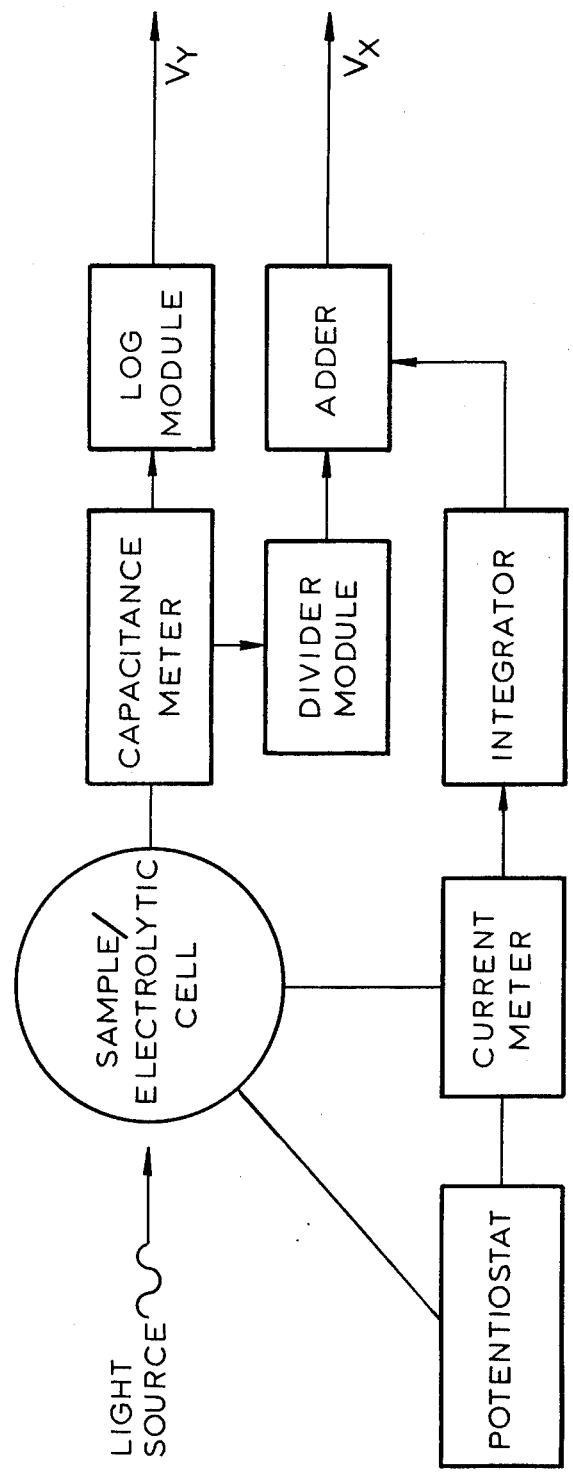
FIG. 1 shows schematically an automatic measuring system of the invention.

FIG. 1 outlines an automatic system for determining donor concentration profiles in samples of semi-conductor epitaxial layer/substrate structures such as are used in IMPATT and other microwave diodes. The sample forms part of an electrochemical cell as will be described hereinafter. The cell is used as part of the feed back path in a potentiostatic circuit, enabling a constant dissolution potential to be maintained, independent of illumination intensity. A filtered 250W quartz-halogen lamp is used to provide illumination in a wavelength region below that of the absorption edge of the semiconductor. The direct current through the cell indicates the dissolution rate, and a current integrator is used to provide a signal proportional to the thickness of material removed, according to Faraday's Law of Electrolysis. The capacitance of the semi-conductor depletion layer, at constant barrier potential, is determined by applying a signal of 50 mV r.m.s. at 3 KHz and measuring the imaginary component of alternating current using a phase sensitive detector in a known manner. This is converted to a signal proportional to the logarithm of donor concentration, which is fed to the Y input of an X-Y recorder.

The simple Schottky relationship between capacitance C and net donor concentration $(N_D - N_A)$ is assumed, viz $$C = \left[ \frac{q(N_D - N_A)\epsilon_o\epsilon}{2} \right]^{\frac{1}{2}} \psi^{\frac{1}{2}} A$$

The barrier height determined by previous capacitance-voltage calibration is typically 1.4 eV for GaAs under our chosen disillusion conditions, and area A is about $5 \times 10^{-2} cm^2$.

The capacitance signal is used to determine the depletion width W, by means of a divider module, since $W = \epsilon_o \epsilon A/C$.

This provides a correction which is added to the determined value of thickness removed by disillusion, to give the effective depth. This is plotted on the X axis of the X-Y recorder.

No special preparation of the sample is required, as the area to be examined is defined by a seating ring on the cell, and contacts to the back of the sample are simple tin-coated probes which are readily secured by means of a voltage pulse. Once dissolution has commenced, the equipment may run unattended until a predetermined amount of the semi-conductor material has been removed.

Figure 2:
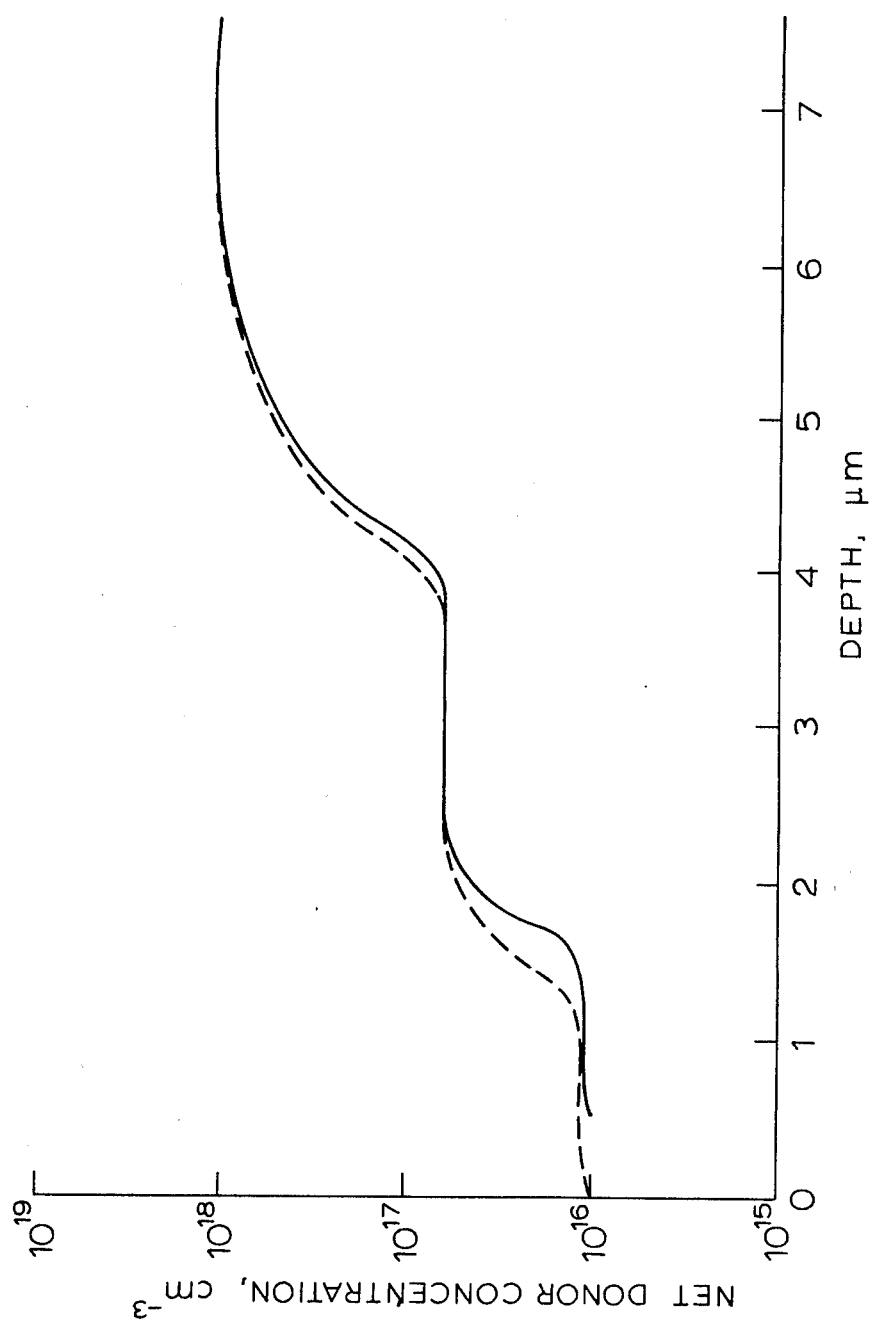
FIG. 2 shows graphically the relationship between net donor concentration per cubic centimeter and depth of profiled surface in microns for a GaAs sample.
Figure 3:
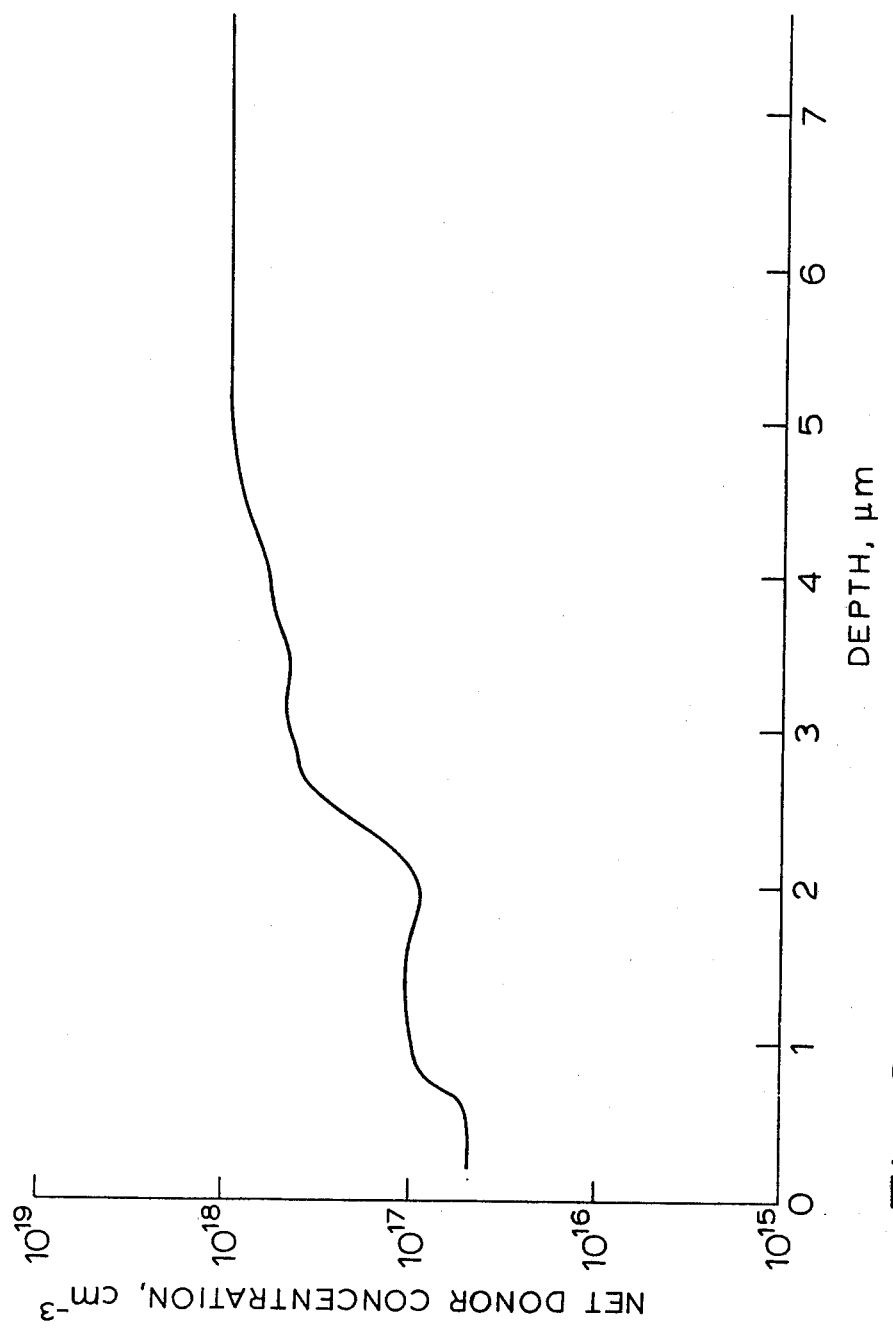
FIG. 3 shows graphically non-uniformity of semiconductor doping, at relatively high doping levels, for a sample produced in an epitaxial growth equipment in which there was a control fault.

An example of a profile obtained for a double epitaxial GaAs structure $(n^-/n/n^+)$ is shown in the continuous plot of FIG. 2. Those skilled in the art will appreciate that it would have been extremely tedious to obtain this profile using a conventional system involving stepetching, bearing in mind that maximum depletion widths before breakdown are about 0.4 $\mu$m and 0.1 $\mu$m at donor concentrations of $10^{17}$ and $10^{18} cm^{-3}$ rspectively. The continuity of measurement given by the present invention is particularly significant where there is non-uniformity of doping at relatively high doping levels, as for the example represented by the curve of FIG. 3. This curve illustrates a situation where a control fault was present in the epitaxial growth equipment, the effects of which are clear from the detailed information provided in the profile. Baxandall, Colliver and Fray, in a paper entitled "An Instrument for the Rapid Determination of Semi-Conductor Impurity Profiles," (J. Phys. E: Sci. Instrum. 1971. 4 pp 213–221) and Copeland, in an article entitled "A Technique for Directly Plotting the Inverse Doping Profile of Semi-Conductor Wafers," (IEEE Trans. Electron Devices 1969 ED–16 pp 445-499) have previously described methods for characterising semi-conductor materials. These prior art methods are most suitable for the examination of low-doped layers of limited thickness. Being of particular value with samples of high doping levels, therefore, the techniques of the present invention may be complementary to those methods.

According to Copeland, his technique "involves driving a Schottky diode deposited on the surface with a small constant RF current (a few hundred microamperes at 5 MHz). The depth of the depletion layer is varied by changing the dc bias, but this is the only role of the dc voltage. The inverse doing profile $n^{-1}(x)$ is obtained by monitoring the voltage across the diode at the fundamental frequency, which is proportional to the depth x, and the second harmonic voltage, which is proportional to $n^{-1}$."

In the system of Baxandall, Colliver and Fray, "a matrix of Schottky barrier diodes is deposited on the surface, contact being made with each diode in turn by a small probe. The probe is fed with a dc bias voltage and a small voltage at 100 kHz, the 100 kHz current flowing in the diode being a measure of the small-signal capacitance $C_x$. Another small voltage, at 1 kHz, is superimposed, and the consequent depth of modulation of the 100 kHz current is a measure of $dC_x/dV$. The impurity concentration N and the depth, are known functions of $C_x$ and $dC_x/dV$, and the instrument does the appropriate analogue computations to provide a direct plot of lg N against depth as the dc reverse-bias voltage is varied."

The prior art methods permit carrier concentration to be determined and plotted automatically as a function of depth, but are limited by the maximum depletion width, that is, that which is reached just before reversed breakdown of the junction takes place. In order to probe more deeply into the material it has heretofore been necessary to combine these measurements with a number of separate chemical etching sets. This procedure is tedious, and a potential source of error, and often leaves gaps in the profile if the etching steps are too coarse. Also, because the maximum depletion width is very small at high doping levels, it has usually been impossible to obtain a continuous profile through the interface between an epitaxial layer and a heavily doped substrate.

The present invention utilizes an electrochemical technique which permits completely automatic continuous profiling to any required depth (including heavily doped regions) the conventional metal Schottky barrier being replaced by a concentrated liquid electrolyte in contact with a well defined area of the semi-conductor surface. This form of contact permits capacitance measurements, as before, and also provides a medium for anodic electrochemical dissolution of the semi-conductor. The disillusion rate depends upon the availability of minority carriers within the semi-conductor, and these may be provided by illumination through the electrolyte - semi-conductor surface. Continuous measurement is thus possible while the semi-conductor is being dissolved under controlled conditions. The anodic dissolution current can be measured and integrated to give the total amount of material removed at any instant. A simple analogue arrangement then enables carrier concentration to be plotted against depth, and this with no material limit.

Apparatus making use of the invention can be fully automated, so that once a sample has been mounted no further attention is required until it has been profiled to the required depth. In a working embodiment of such apparatus the full scale depth is variable in steps between 1.8 $\mu$m and 72 $\mu$m and there is a control unit programmed so that, when full scale is reached, either the system is switched off so that disillusion stops or the recorder is automatically recycled. With recycling, of course, the depth range can be extended indefinitely.

The apparatus can be used to characterize by profile a variety of epitaxial layer/substrate structures of n-type gallium arsenide and gallium phosphide, and structures which contain p-n semi-conductor junctions, as well as other materials.

Figure 4:
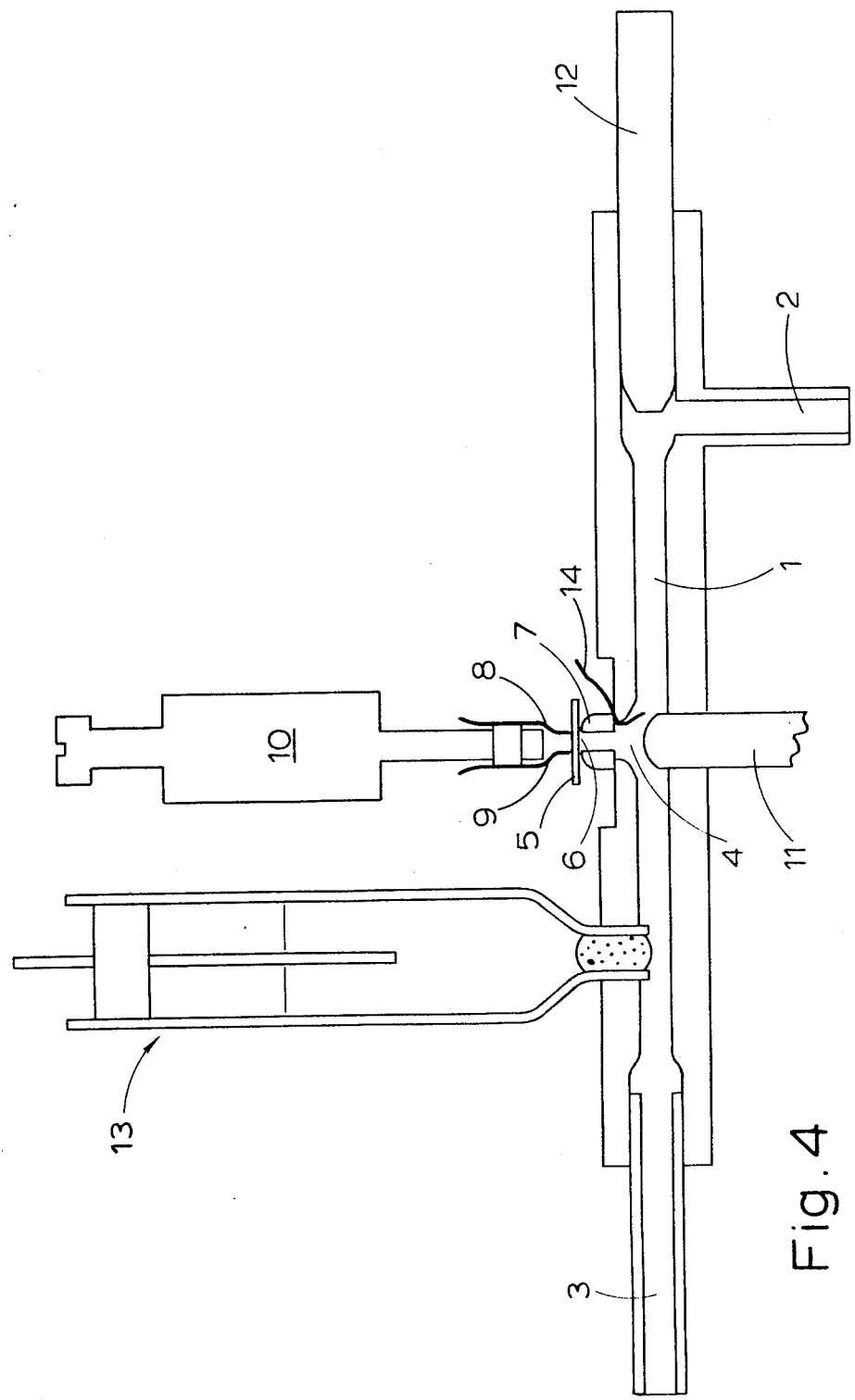
FIG. 4 shows an electrochemical cell of the system of FIG. 1.

Referring now to FIG. 4, the electrolytic cell shown therein comprises a flow passage 1 between an electrolyte input pipe 2 and an output pipe 3. The passage 1 is formed in a tube of PTFE. An orifice 4 in the passage 1 is closed by a sample 5 of material to be tested so that a face 6 of the sample 5 is exposed to electrolyte in the passage 1.

A seal against the egress of electrolyte is provided between the face 6 and the passage 1 and in the illustrated embodiment this seal takes the form of a PVC mounting ring 7. The sample 5 is held in place against the mounting ring 7 by gold alloy wire springs 8 and 9 which also provides electrical contact with the sample 5. The spring contacts 8 and 9 are backed up by a contact plunger arrangement indicated at 10 which maintains sealing pressure of the face 6 against the mounting ring 7.

Directly opposite and facing the orifice 4 is a light pipe 11 by means of which the face 6 of the sample 5 can be illuminated from a variety of light sources. The mounting ring 7 is so arranged as to define closely the area of face 6 which is subject to illumination by way of the light pipe 11.

The working cathode of the electrochemical cell is provided by a spectrographically pure carbon electrode 12 received in one end of the passage 1. Also received in the passage 1, towards the other end thereof, is a reference electrode indicated at 13. This reference electrode 13 is a saturated calomel electrode of the porous plug type.

A measurement electrode 14 extends past mounting ring 7, through orifice 4 and thence into passage 1. This measurement electrode consists of a platinum wire and is used for capacitance measurements to reduce the influence of electrolyte series impedance to a negligible level.

The cathode 12 and electrodes 13 and 14 are in contact with the electrolyte in the passage 1. The electrolyte is a 10% w/v aqueous KOH solution prepared from "analytical grade" reagent with minimum exposure to the atmosphere. It is maintained and pumped through the cell under a pressure of "white spot" nitrogen, to minimise oxygen and carbon dioxide contamination. In use, the flow rate of the electrolyte is 0.02 ml s$^{-1}$, and before use "white spot" nitrogen is bubbled through the reservoir, not shown, of electrolyte to remove contamination therefrom. It will be appreciated that the action of the electrolyte in the passage 1 will cause the progressive removal of material from the face 6 of the sample 5. Furthermore, there will be anodic polarisation of the sample 5 so that when the face 6 is subjected to illumination by way of the light-pipe 11 an electrostatic potential will be set up. The electrostatic potential will vary with the depth of sample which, as already stated, is progressively altered by the electrolytic action.

Figure 5A:
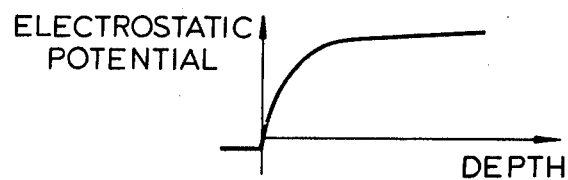
FIG. 5a shows graphically the relationship between electrostatic potential and depth of sample for an illuminated sample as shown in FIG. 5b.
Figure 5B:
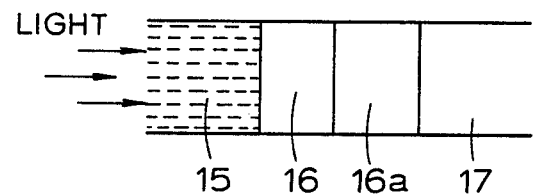

The relationship between electrostatic potential and depth for an illumination sample is illustrated by FIG. 5. As shown in the theoretical model illustrated in FIG. 5b, light is transmitted through the electrolyte 15 onto the face 6 of the sample. The face 6 forms a boundary of a depletion region 16. A quasi-neutral diffusion region 16a separates the depletion region 16 from the bulk semi-conductor 17.

Myamlin and Pleskov, in a book entitled "Electrochemistry of Semi-Conductors" (Plenum Press, 1968) have shown how the model of FIG. 5b may be analysed to yield the relationship between electrostatic potential and depth as shown in FIG. 5a.

Figure 6:
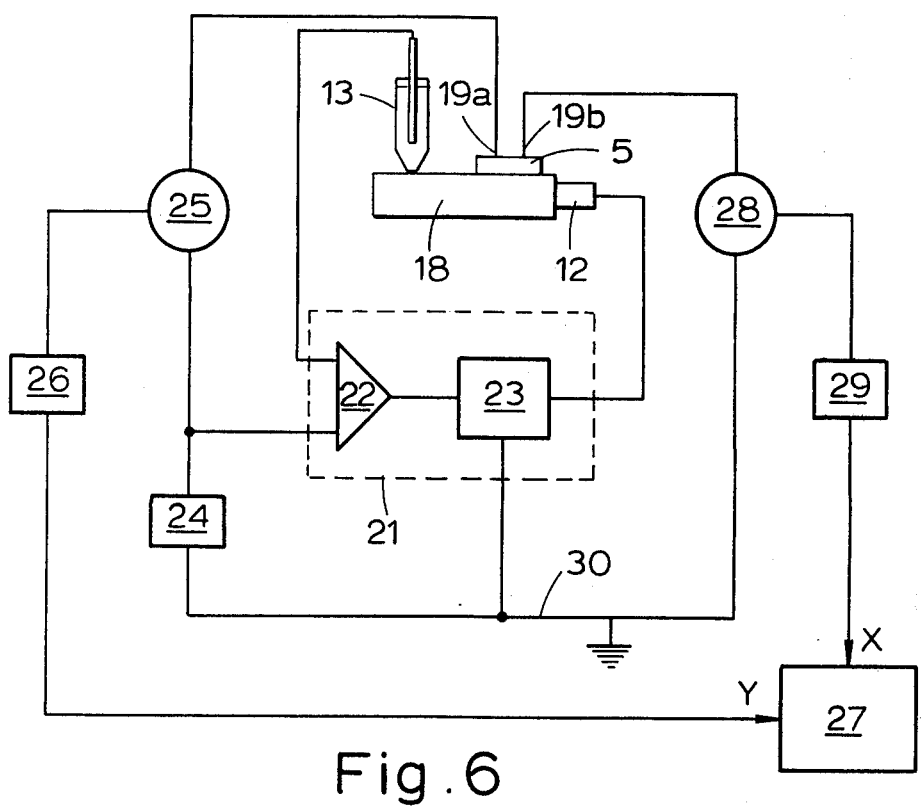
FIG. 6 shows a block diagrammatic form the measurement circuit of the system of FIG. 1 in greater details.

The operation of the aforedescribed system may be understood more readily from FIG. 6. In FIG. 6, the electrolytic cell is of FIG. 4 is indicated generally at 18. The semi-conductor sample 5 is supported on the cell 18 and has two point contacts 19a and 19b. (Preferably, of course, cell 18 is of the form illustrated in FIG. 4 wherein the point contacts 19a and 19b may be provided by springs such as those indicated at 8 and 9 in FIG. 4. A potentiostat illustrated generally by the broken outline 21 is formed by a differential input amplifier 22 the output of which drives a current source 23. The output from the current source is connected to the carbon working electrode 12, which is in contact with the electrolyte in the cell 18. One of the inputs to the amplifier 22 is coupled directly to the saturated calomel electrode 13 and the other input to the amplifier 22 is coupled to a voltage sweep generator 24 which is also coupled to a high impedance voltmeter 25 and to the contact 19a. The volt meter 25 is coupled by way of unit 26 to the Y input of an X-Y pen recorder 27. The X input to the recorder 27 is derived from a unit 29 and a logarithmic microammeter 28. The microammeter 28 is connected between the back contact 19b and an earth line 30.

The potentiostat 21 is used to regulate the current passed through the sample 5 so that the potential between the sample and the reference electrode 13 is held as close as possible to that set on a reference voltage source. The generator 24 sweeps the reference voltage over the desired range. In order to eliminate as far as possible the effect of the resistive potential drop at the sample contact, the contacts 19a and 19b provide separate current and voltage contact points, and the cell potential is measured independently of the grounded swept voltage generator 24, by using a high impedance volt meter 25. The logarithmic microammeter 28 is incorporated in the circuit so that semi-logarithmic voltage-current curves can be directly plotted using X-Y recorder 27. A digital integrator used to measure the time integral of the disillusion current during the anodic stripping of epitaxial layers.

The arrangements can provide pulse signals to initiate automatic plotting of voltage-current at predetermined intervals of depth of material removed.

This arrangement has been used successfully to profile GaAs and epitaxial GaP structures at depths of as much as 50 $\mu$m. The system measures an effective mean value of donor concentration over the whole depletion width. Since the depletion width depends upon doping level and potential barrier height, depth resolution is significantly limited at the lowest donor concentrations plotted. Such is demonstrated in FIG. 2, where there is uncertainty represented by the difference between the continuous plot (which includes a depth scale correction equal to the total depletion layer width) and the broken line (where this correction is omitted.)

Another effect which assumes importance at low values of donor concentration is the influence of the capacitance of any deep trap levels which may be present. A proportion of these may be ionised in the near-surface region of the depletion layer, resulting in an over-estimate of shallow donor concentration. For example, the donor concentration of the active layer of the sample depicted in FIG. 2 was quoted by our suppliers as $7 \times 10^{15} cm^{-3}$.

We believe however, that neither of these limitations is inherent to the use of an electrolyte to form the Schottky barrier medium. Accordingly, we have devised a capacitance analysis, employing modulation techniques, to give improved depth resolution, with the added possibility of separate plotting of shallow donor and deep donor concentrations. The refinement is illustrated by the improved system depicted in FIG. 7.

Figure 7:
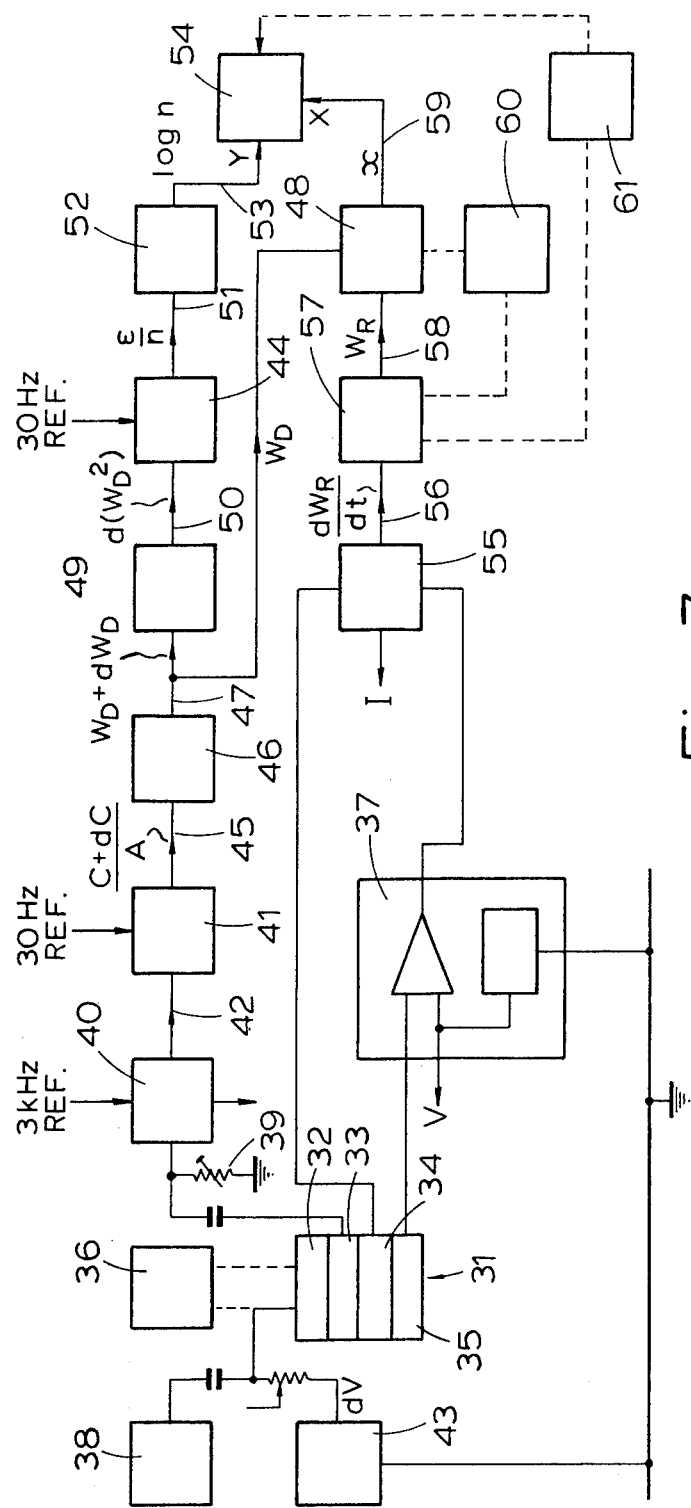
FIG. 7 shows in block schematic form an improved measuring system according to the invention.

In FIG. 7, the electrochemical cell of FIG. 4 is indicated at 31. (It will be understood, of course, that the representation of cells 31 and of the other elements of FIG. 7 bears no resemblance to the actual construction). The cell 31 includes the sample 32, an ac cathode 33, a dc cathode 34 and a saturated calomel electrode 35. Probe contacts to the back of the sample 32 are made by way of a contact maker 36, which conveniently includes springs such as the springs 8 and 9 of FIG. 4.

As with the system of FIG. 6, a potentiostat 37, employing a single integrated circuit operational amplifier, is used to maintain a constant anodic dissolution potential. The required potential is set on a built-in voltage reference source, and the potentiostat 37 controls the current through the cell so that the same potential appears at the saturated calomel reference electrode 35. The response time of the potentiostat is arranged to be greater than 100 ms to permit external modulation of the cell potential for differential capacitance measurements, as will be described hereinafter. (The value of anodic potential must lie within a safe range wherein premature breakdown will not occur, thus to avoid preferential disillusion at regions of material imperfections. For gallium arsenide, we choose a value of −0.3V, relative to the calomel electrode 35, which corresponds to a total band-bending of about 1.5V — an effective reverse bias of about 0.5V.

To enable the rest potential of the sample to be checked, the potentiostat 37 incorporates switch-controlled relays permitting the cathode to be disconnected so that the rest potential may be checked. Initially, connection is made to the contact maker 36 and the relays are then switched to the standby position in which the cathode is disconnected. Having done this, dissolution is initiated by the completion of all connections between the cell 31 and the potentiostat 37 and the removal of a shutter of the illumination source (not shown in FIG. 7). It will be appreciated that since only n-type material has a rest potential sensitive to illumination, the checking of this rest potential in each case permits the conductivity-type of the sample to be determined prior to dissolution. Also, it is recommended that the relays be controlled by an arrangement including fail-safe protection against disruption of the power supply.

A 3 kHz oscillator 38 applies a 50 mV rms signal to the sample 32. A variable resistor 39 is arranged in series with the sample 32 to provide a current path therethrough. The resistor 39 is pre-set, for sensitivity calibration, and has an impedance (some tens of ohms) which is negligible compared with the lowest sample impedance at 3 kHz. To determine the depletion layer capacitance, a 3 kHz phase sensitive amplifier 40 detects the signal across resistor 39.

For convenience, fully encapsulated modules are used for both oscillator 38 and amplifier 40, with the addition of a simple phase-adjust circuit based on an integrated circuit operational amplifier.

The phase and sensitivity of the phase sensitive amplifier 40 are adjusted using a standard test capacitor, of capacitance of the order of 10 nF, to give an output representative of the capacitance per unit area, C/A, of the sample 32. It will be appreciated that to effect this requires a knowledge of the area A which is exposed to illumination and is thereby dissolved during analysis of the sample. However, by use of a travelling microscope, we have established that this area is highly reproducible in the apparatus.

It may here be remarked that the area A may be surrounded by a ring of "excess" area $A_E$ which is exposed to the electrolyte but is not subject to illumination. Careful design of the mounting arrangement for the sample 32 (for example, by use of a mounting ring such as is shown at 7 in FIG. 4) can reduce this excess area, possibly to negligible proportions. In any event, it may be assumed that before disillusion commences, the "excess" capacitance attributable to the excess area $A_E$ is related to the total capacitance measured in the same ratio as the excess area $A_E$ bears to the total area, provided that there is lateral uniformity of doping. Accordingly, to compensate for the effect of the excess area $A_E$, we provide compensation means 41 which allows the output, indicated at 42, of the phase sensitive amplifier 40 to be offset by an appropriate fraction of the initial output, measured with the sample in darkness, prior to any dissolution.

At the sample 32, the depletion width is modulated by means of a 30 Hz Wein Bridge oscillator 43 connected in the return circuit path from the potentiostat 37. The Wein Bridge oscillator 43 gives an output dV which is influenced by losses via the connection to oscillator 38 and is set at 100 mV rms. Thus, it will be understood, there is a 30 Hz component, which may be termed $dC/A$, in the dc output 42 of the 3 kHz phase sensitive amplifier 40. In the same way as with the component corresponding to C/A, this component $dC/A$ must similarly be offset to account for any contribution from the excess area $A_E$. This is accomplished by adding a 30 Hz offset, with 180° phase difference, derived from the Wein Bridge oscillator 43 by way of a phase-shifter circuit. The adjustment is performed with the output of the compensation means 43 temporarily connected to a 30 Hz phase sensitive amplifier 44, to be described hereinafter. In compensating the output representing both C/A and $dC/A$, these outputs are monitored on a four figure digital volt meter, not shown. The compensated signals representing C/A and $dC/A$ (which latter remains as a 30 Hz component), indicated at 45, are fed into a divider unit 46. The divider unit 46 is based upon an encapsulated analogue divider module and provides an output 47 representative of the depletion width $W_D$ (with a superimposed component $dW_D$) as derived from the equation:

$$W_D = \epsilon_o \epsilon A/C$$

It will be understood that the divider unit 46 is calibrated using a known or a previously ascertained value of relative permittivity — that is, dielectric constant — $\epsilon$ of the semi-conductor.

The output 47 is effectively split so that its component $W_D$ goes to an adder 48, to be discussed later, and its component $dW_D$ is operated upon by an analogue squarer unit 49. The squarer unit 49 consists of an encapsulated module requiring no external adjustment and provides an output at 30 Hz which is proportional to $d(W_d^2)$. This output, indicated at 50, is converted to a dc voltage by the 30 Hz phase sensitive amplifier 44. The amplifier 44 is purpose built to have high sensitivity with an ultra-low drift, low offset, integrated circuit operational amplifier output stage with a usable dynamic range of $10^4$. This provides for a carrier concentration span, in the sample, of $10^4$ (for example $10^{15}$ to $10^{19}$ cm$^{-3}$) as given by the equation:

$$n = \frac{2\epsilon_o \epsilon}{q} \cdot \frac{dV}{d(W_D)^2}$$

As will be described hereinafter, the gain of the 30 Hz phase sensitive amplifier 44 can be set by a calibration procedure so that the output voltage 51 represents $\epsilon/n$. The output voltage 51 is fed into a logarithmic amplifier 52 based on an encapsulated module. The logarithmic amplifier 52 is calibrated to take account of the relative permittivity for the sample so as to provide an output voltage 53 which is proportional to log n. This output voltage 53 is applied to the Y-axis input of an X-Y pen recorder 54.

Having outlined the derivation of differential capacitance in the system of FIG. 7, we shall now describe how this is related to depth.

The anodic dissolution current is measured using a differential input current meter 55. The meter 55 is purpose-built using four integrated circuit operational amplifiers and is calibrated to provide an output 56 representative of the dissolution rate $dW_R/dt$, that is, the thickness of material removed per unit of time. Calibration of the current meter 55, which takes into account various parameters including those of the sample material and the area A of dissolution, is based on the equation:

$$W_R = \frac{M}{NFDA} \int I \cdot dt$$

The output signal 56 from the current meter 55 is fed to an integrator 57 which, in known manner, provides an output 58 representative of the total thickness $W_R$ removed by dissolution at any time. In the adder 48, this output 58 representative of $W_R$ is added to that component of the output 47 which is representative of the depletion width $W_D$, thus to provide an output 59 representative of the effective total depth $x$. Output 59 is applied to the X-axis input of the X-Y recorder 54 so that, in use, the X-Y recorder 54 plots log n against $x$.

The integrator 57 has its input sensitivity variable by means of a switch, not shown, to allow for different values of maximum ("full scale") depth. In our own apparatus, the full scale depth has 6 permissible values from 1.8 $\mu$m to 72 $\mu$m. A control unit 60 is arranged to sense when the selected full scale depth has been reached, and may be set either to switch off the system at this time, in which case dissolution stops, or to perform a further complete cycle by returning the recorder pen to the beginning of the X scale. In this latter mode of operation, of course, the total depth attainable is extended indefinitely.

For convenience, the output 58 from integrator 57 is stepped by means of a stepping-motor-driven, multiturn potentiometric output stage, thus to permit long integration periods. The integration periods may be as much as several hours long and, in our apparatus, the integrator output is stepped approximately 360 times during a complete plot to full scale depth. For each step, the pen of X-Y recorder 54 is arranged to register a single point, the pen having a lowering mechanism controlled from the integrator 57 by a control unit 61.

To enable the dissolution depth $W_R$ to be checked at any time during plotting, a switch, not shown, is provided to remove the depletion width correction $W_D$ from output 59.

It is believed that those skilled in the art will appreciate how the integrator 57 and the parts of the system associated therewith may be simply calibrated by applying dc test inputs and using a digital volt meter to measure output values. Calibration of the parts of the system used to measure depletion width is similarly straightforward, at least up to the output of the divider 46, involving merely reference to a fixed test capacitor and dc measurements. In calibration of the 30 Hz phase sensitive amplifier 44, it is convenient to avoid attempting to make accurate measurements of ac signal levels (at 30 Hz). This can be done by effecting a final adjustment of phase and gain of amplifier 44, using an actual semi-conductor specimen, in a manner now to be described.

The specimen should be a uniformly doped slice, with a doping level of about $10^{17}cm^{-3}$, so as to lie about midway on the logarithmic scale. The precise value need not be known in advance, as this is measured using the electrochemical system. It is first verified that the dark current (that is, with no illumination,) is negligible at the usual dissolution potential, to ensure that no significant conductance component will be present to interfere with the measurement. The 3 kHz power sensitive amplifier 40 have five switched ranges for capacitance measurements and accordingly can be used to measure the capacitance for a given reference potential. By sweeping the reference potential over a range of about 0.5 V, and plotting this against the capacitance measured by the 3 kHz power sensitive amplifier 40, a C-V plot is obtained, from which the carrier concentration can be determined by curve fitting. This is the technique used with the system of FIG. 6, and involves matching the experimental curve to a theoretical curve derived from the well-known Schottky barrier formula for depletion layer capacitance.

The gain of the 30 Hz power sensitive amplifier 44 is adjusted until the derived value of carrier concentration n is reproduced on the X-Y recorder 54. Phase correction is performed at the same time, whilst the detector stage output of amplifier 44 is monitored on an oscilloscope. It is, of course, necessary to apply the aforedescribed excess area compensation to the signal levels during this procedure.

Having calibrated the system in this way, the specimen may be stripped sufficiently to confirm the original assumption that carrier concentration was, at least in the near-surface region, uniform with depth, as is required for successful use of the curve fitting technique. If this proves not to be the case, of course, the calibration procedure may be performed again using another specimen. Once the system has been calibrated in this manner, analysis of n-type samples of the same semiconductor is extremely simple. Loading, contact making and area compensation corrections take only a few minutes, and once dissolution has commenced no further attention is necessary, the system being controlled automatically either to switch off or to recycle when full scale depth has been attained. With GaAs we have worked at dissolution rates of about 2 $\mu$m per hour, so that if relatively thick samples are being analysed it is convenient to let the system run overnight.

To analyse material over similar depths, the prior art methods of Copeland and Baxandall et al would require a laborious procedure of measurement and chemical step etching. These prior art methods rely upon probing in depth by increasing the applied reverse bias and extending the depletion width to the limit determined by reverse breakdown, when further etching is required. The present invention provides a reliable continuous process by its novel use of an electrolytic barrier medium. Although the principle of differential capacitance analysis is the same as that of Baxandall et al, the system design differs somewhat in order to take full advantage of the electrochemical method of the present invention. In particular the system has a wide dynamic range in carrier concentration measurement, to allow a single continuous plot to cover the whole range of concentration encountered in a device structure, without adjustment. In essence, this is achieved by performing the analogue operations on the 30 Hz signal, rather than detecting it at an earlier stage.

A significant advantage of the arrangement of FIG. 7 over the simpler system of FIG. 6 is the improved depth resolution. In some cases, for example, the simpler system could not resolve adequately undulations in carrier concentration at an interface between active and buffer layers in a sample. The resolution of the improved system of FIG. 7 is limited by the Debye Length, which is a factor of ten smaller than the depletion widths which determine the resolution of the simpler system. This may be especially important in checking samples for particular applications.

Other considerations to be borne in mind in use of the invention are the manner and area of illumination. It will be understood that uniformity of illumination across the area examined is essential for a uniform rate of dissolution. At present, we use a multiple fibre light pipe, which gives a uniformity of illumination which is quite acceptable for most purposes. Naturally, however, there will be some spread of light away from the ends of the fibre, which will limit resolution of sharp interfaces at comparatively large depth. It may be possible to effect some improvement in this respect by the use of microscope optic techniques.

We test samples over an area of about 4 mm diameter. It may not be practicable to reduce this area overmuch because of the risk of the ratio between the excess area and the disolved area becoming excessively large, when errors in compensation could reduce the accuracy of plotting, particularly in the case of an interface between areas of high and low concentrations. In certain cases, it might be advantageous to employ an in-contact mask, but this would complicate the system.

At the flux used, the influence of the illumination upon the carrier concentration measurement is apparently negligible. The external photopotential is accommodated by the potentiostat, although there remains a small increase in measured capacitance (typically less than 10%) at a given anodic potential when the illumination is applied.

Thus there appears to be a decrease in impedance in the region very near to the surface in which the light is absorbed. However, no change can be detected in the apparent value of carrier concentration derived from the modulation of depletion width, in regions of uniform doping. We have, though, observed some apparent change at excessively high illumination levels such as occur when the light source is not closely filtered.

In the analysis of gallium arsenide, a quartz iodine tungsten light source is used, with a narrow band filter at 550 nm. For gallium phosphide, this is substituted by a blue-filter mercury arc illumination source.

With minor modifications, the system and technique is suitable for the analysis of p-type material, and hence structures containing p-n junctions may also be analysed.

We claim:

1. Apparatus for determining the carrier concentration as a function of depth in a semiconductor material by measuring the capacitance of a Schottky diode depletion layer formed in the semiconductor, said apparatus comprising an electrolytic cell arranged to contain electrolyte, means for mounting the semiconductor material in the cell so that a surface of the semiconductor can contact the electrolyte, the junction of said semiconductor and electrolyte forming said Schottky diode and said electrolyte in use progressively etching the surface area of the semiconductor material, masking means defining an area of the semiconductor material in contact with the electrolyte, electrical contact means for contacting the semiconductor, means for applying a d.c. voltage to said electrical contact means, electrode means for applying a d.c. voltage to said electrolyte, means for measuring the d.c. current through the electrolyte, means for applying an a.c. voltage to said Schottky diode, and a capacitance measuring unit responsive to said a.c. voltage for measuring the capacitance of the depletion layer of the Schottky diode.

2. Apparatus according to claim 1, including means connected to said capacitance measuring unit for providing a measurement of the carrier concentration of the semiconductor material.

3. Apparatus according to claim 2, including an integrator for integrating the current flowing through the electrolyte.

4. Apparatus according to claim 3, including an X - Y recorder which is coupled to said measuring means and to said integrator to provide a continuous graphical plot of the relationship between donor concentration at the surface of the Schottky diode and the thickness of the semiconductor edged from said area.

5. Apparatus according to claim 1, wherein said capacitance measuring means includes means for measuring the differential capacitance of the depletion layer.

* * * * *